(12) United States Patent
Liu et al.

(10) Patent No.: US 9,556,420 B2
(45) Date of Patent: Jan. 31, 2017

(54) SPECIALIZED (ISO)EUGENOL-4-O-METHYLTRANSFERASES (S-IEMTS) AND METHODS OF MAKING AND USING THE SAME

(71) Applicant: Brookhaven Science Associates, LLC, Upton, NY (US)

(72) Inventors: Chang-Jun Liu, Rocky Point, NY (US); Yuanheng Cai, Ridge, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 255 days.

(21) Appl. No.: 14/306,511

(22) Filed: Jun. 17, 2014

(65) Prior Publication Data

US 2014/0370568 A1 Dec. 18, 2014

Related U.S. Application Data

(60) Provisional application No. 61/836,177, filed on Jun. 18, 2013.

(51) Int. Cl.
  *C12N 9/10* (2006.01)
  *C12N 15/82* (2006.01)

(52) U.S. Cl.
  CPC ......... *C12N 9/1007* (2013.01); *C12N 15/8255* (2013.01); *C12Y 201/01146* (2013.01)

(58) Field of Classification Search
  None
  See application file for complete search history.

(56) References Cited

U.S. PATENT DOCUMENTS 7,514,596 B2 * 4/2009 Chiang ................ C12N 9/0006
  800/278
8,889,392 B2 * 11/2014 Liu ...................... C12N 9/1007
  435/193

FOREIGN PATENT DOCUMENTS

WO  WO 9850570 A2 * 11/1998 ........... C12N 9/1007
WO  WO 03105723    12/2003

OTHER PUBLICATIONS

Bhuiya, M., et al., "A Cost-Effective Colorimetric Assay for Phenolic 0-methyltransferases and Characterization of Caffeate 3-0-Methyltransferases from Populus trichocarpa," Analytical Biochemistry, vol. 384, pp. 151-158, 2009.

Bhuiya, M., et al., "Engineering Monolignol 4-0-Methyltransferases to Modulate Lignin Biosynthesis," The Journal of Biological Chemistry, vol. 285, No. 1, pp. 277-285, 2010 and supplementary material pp. 1-9 [ online] [retrieved Oct. 28, 2010 from: <URL:htto://www.ibc.org/content/suDD112009/10/29/M109.036673.DCI.html>].

Brookhaven National Laboratory News Release, "Making New Enzymes to Engineer Plants for Biofuel Production," No. 1021, pp. 1-2, Dec. 21, 2009, [online] [retrieved May 30, 2012 from: <URL:http://www.bnl.gov/bnlweb/pubaf/pr/PR print.asp?prID= 1021>].

Brookhaven National Laboratory News Release, "Scientists Unravel More Details of Plant Cell-Wall Construction;" No. 1209, pp. 1-3, Dec. 13, 2010, [online] [retrieved May 30, 2012 from: <URL: http://www.bnl.gov/bnlweb/pubaf/pr/PR print.asp?prID= 1209> ].

Chapple, C., et al., "Loosening Lignin's Grip on Biofuel Production," Nature Biotechnology, vol. 25, No. 7, DD. 746-748, 2007.

Somerville, C., "Biofuels," Current Biology, vol. 17, No. 4, pp. R115-R119, 2007 [online] [retrieved May 7, 2013 from: <URL:http://www.sciencedirect.com/science/article/pii/S0960982207008 I 11>].

Wang, J., et al., "Characterization of S-Adenosyl-L-Methionine: (Iso )eugenol 0-Methy Itransferase Involved in Floral Scent Production in Clarkia breweri," Archives of Biochemistry and Biophysics, vol. 349, No. I, pp. 153-160, 1998.

Wang, J.,-et al., "Identification of Specific Residues Involved in Substrate Discrimination in Two Plant 0-Methyltransferases," Archives of Biochemistry and Biophysics, vol. 368, No. 1, pp. 172-180, 1999.

\* cited by examiner

*Primary Examiner* — Jason Deveau Rosen
(74) *Attorney, Agent, or Firm* — Dorene M. Price

(57) ABSTRACT

Specialized (iso)eugenol 4-O-methyltransferase (s-IEMT) enzymes having increased capacity for methylation of monolignols are disclosed. The s-IEMTs have unique activity favoring methylation of coniferyl alcohol versus sinapyl alcohol. Various s-IEMTs methylate ferulic acid. Means for producing the various s-IEMTs are provided. The s-IEMTs are useful for modification of lignin content and production of aromatic compounds.

12 Claims, No Drawings

SEQUENCE LISTING

<160> NUMBER OF SEQ ID NOS: 1

<210> SEQ ID NO 1
<211> LENGTH: 368
<212> TYPE: PRT
<213> ORGANISM: Clarkia breweri

<400> SEQUENCE: 1

```
Met Gly Ser Thr Gly Asn Ala Glu Ile Gln Ile Pro Thr His Ser
1               5                   10                  15

Ser Asp Glu Glu Ala Asn Leu Phe Ala Met Gln Leu Ala Ser Ala Ala
                20                  25                  30

Val Leu Pro Met Ala Leu Lys Ala Ala Ile Glu Leu Asp Val Leu Glu
            35                  40                  45

Ile Met Ala Lys Ser Val Pro Pro Ser Gly Tyr Ile Ser Pro Ala Glu
    50                  55                  60

Ile Ala Ala Gln Leu Pro Thr Thr Asn Pro Glu Ala Pro Val Met Leu
65                  70                  75                  80

Asp Arg Val Leu Arg Leu Leu Ala Ser Tyr Ser Val Val Thr Tyr Thr
                85                  90                  95

Leu Arg Glu Leu Pro Ser Gly Lys Val Glu Arg Leu Tyr Gly Leu Ala
            100                 105                 110

Pro Val Cys Lys Phe Leu Thr Lys Asn Glu Asp Gly Val Ser Leu Ala
        115                 120                 125

Pro Phe Leu Leu Thr Ala Thr Asp Lys Val Leu Leu Glu Pro Trp Phe
    130                 135                 140

Tyr Leu Lys Asp Ala Ile Leu Glu Gly Gly Ile Pro Phe Asn Lys Ala
145                 150                 155                 160

Tyr Gly Met Asn Glu Phe Asp Tyr His Gly Thr Asp His Arg Phe Asn
                165                 170                 175

Lys Val Phe Asn Lys Gly Met Ser Ser Asn Ser Thr Ile Thr Met Lys
            180                 185                 190

Lys Ile Leu Glu Met Tyr Asn Gly Phe Glu Gly Leu Thr Thr Ile Val
        195                 200                 205

Asp Val Gly Gly Gly Thr Gly Ala Val Ala Ser Met Ile Val Ala Lys
    210                 215                 220

Tyr Pro Ser Ile Asn Ala Ile Asn Phe Asp Leu Pro His Val Ile Gln
225                 230                 235                 240

Asp Ala Pro Ala Phe Ser Gly Val Glu His Leu Gly Gly Asp Met Phe
                245                 250                 255

Asp Gly Val Pro Lys Gly Asp Ala Ile Phe Ile Lys Trp Ile Cys His
            260                 265                 270

Asp Trp Ser Asp Glu His Cys Leu Lys Leu Leu Lys Asn Cys Tyr Ala
        275                 280                 285

Ala Leu Pro Asp His Gly Lys Val Ile Val Ala Glu Tyr Ile Leu Pro
    290                 295                 300

Pro Ser Pro Asp Pro Ser Ile Ala Thr Lys Val Val Ile His Thr Asp
305                 310                 315                 320

Ala Leu Met Leu Ala Tyr Asn Pro Gly Gly Lys Glu Arg Thr Glu Lys
```

|  |  |  |  | 325 |  |  |  | 330 |  |  |  | 335 |  |
|--|--|--|--|--|--|--|--|--|--|--|--|--|--|
| Glu | Phe | Gln | Ala | Leu | Ala | Met | Ala | Ser | Gly | Phe | Arg | Gly | Phe | Lys | Val |
|  |  |  | 340 |  |  |  |  | 345 |  |  |  |  | 350 |
| Ala | Ser | Cys | Ala | Phe | Asn | Thr | Tyr | Val | Met | Glu | Phe | Leu | Lys | Thr | Ala |
|  |  | 355 |  |  |  |  | 360 |  |  |  |  | 365 |

SPECIALIZED (ISO)EUGENOL-4-O-METHYLTRANSFERASES (S-IEMTS) AND METHODS OF MAKING AND USING THE SAME

CROSS-REFERENCE TO RELATED APPLICATIONS

This application claims the benefit of U.S. Provisional Application No. 61/836,177, filed on Jun. 18, 2013, the entire contents of which are incorporated herein by reference.

GOVERNMENT SUPPORT

This invention was made with Government support under contract number DE-AC02-98CH10886, awarded by the U.S. Department of Energy. The Government has certain rights in the invention.

BACKGROUND

Lignin, the most abundant terrestrial biopolymer after cellulose, imparts structural integrity to the plant cell wall. While it is important for plant viability it impedes efficient use of woody biomass for biofuel production. Lignification increases the difficulty and energy costs of degrading the polysaccharide in the cell wall to simple fermentable sugars, thereby thwarting efficient ethanol production. Increased understanding of lignin biosynthesis and efficiently managing plant lignification will greatly facilitate the efficient generation of feedstocks for bioenergy and chemical, production.

The small molecule phenolic compounds that impinge upon or directly participate in lignin biosynthetic pathways also possess significant biological activities that are beneficial to humans. For example, their capacity to act as antioxidants is relevant to health issues such as cancer, cardiovascular and neurodegenerative diseases. These aromatic compounds are useful as flavorings in the food industry and are increasingly useful in cosmetic preparations, both as skin protectants as well as for their olfactory impacts.

Comparative structure-function analysis had revealed a detailed understanding of the basis for the regioselective O-methylation of lignin monomeric precursors and for other phenylpropanoids. A set of novel molecular tools, namely, modified (iso)eugenol-4-O-methyltransferases (m-IEMTs) (also called monolignol 4-O-methyltransferases or MOMTs) that may be effective for manipulation of lignin content and composition in plants have been generated. Particularly, m-IEMTs were created that specifically 4-O-methylate both the G- and the S-lignin precursors and modulate lignin content when expressed in transformed plants (Liu, et al., U.S. patent application publication US2012/117694A1, the entire contents of which are incorporated herein by reference).

In efforts to further develop 4-O-methyltransferases for lignin modification as well as for their potential to generate industrially useful chemicals and chemical feedstocks, specialized (iso)eugenol-4-O-methyltransferases (s-IEMTs) (which may also be identified herein as specialized monolignol-4-O-methyltransferases: s-MOMTs) that display specific preference for the G-lignin precursor p-coniferyl alcohol are provided. Some of the specialized (iso)eugenol-4-O-methyltransferases have enhanced activity for 4-O-methylation of ferulic acid and others for generation of iso-sinapyl alcohol from 5-hydroxyl coniferyl alcohol.

DESCRIPTION

Starting with a modified (iso)eugenol-4-O-methyltransferase (m-IEMT) previously designated MOMT-5 having the five substitutions Leu for Thr at 133, Ile for Glu at 165, Ile for Phe at 175, Trp for Phe at 166 and Phe for His at 169 (T133L/E165I/F175I/F166W/H169F), where the amino acid residue numbers correspond to those for the *C. breweri* (iso)eugenol-4-O-methyltransferase protein (SEQ ID NO. 1), the synergistic effects of simultaneously modifying adjacent amino acids located in the substrate binding pocket have been explored. Specialized (iso)eugenol-4-O-methyltransferases (s-IEMTs) were generated that have relatively little activity on sinapyl alcohol compared to activity on p-coniferyl alcohol. Some species of s-IEMT have enhanced activity toward 4-O-methylation of ferulic acid. Additional species of s-IEMT have the capacity to generate iso-sinapyl alcohol. These s-IEMTs are useful for altering lignin precursors in plants, altering lignin composition in plants, and for producing potentially useful chemicals and chemical feedstock in plants as well as in different heterologous expression systems.

The Combinatorial Active-site Saturation Test (CAST) first described by Reetz, et al. (Angew. Chem. Int. Ed. 2005, 44:4192-4196) was used to examine additional amino acids in the substrate binding pocket of MOMT-5, an m-IEMT generated previously, to generate libraries of mutants from which the s-IEMT proteins were selected.

Embodiments include various specialized (iso)eugenol-4-O-methyltransferases (s-IEMTs) that exhibit a specificity bias for 4-O-methylation of coniferyl alcohol in comparison to methylation of sinapyl alcohol. Incorporation, in expressible form, of the genes encoding the specialized (iso)eugenol-4-O-methyltransferases in plants provides the opportunity to modify the structure and the content of lignin in the maturing and mature transgenic plants. Thus, additional embodiments described herein include genes encoding the s-IEMTs, constructs for expression of the genes and plants transformed with the expression constructs. Further embodiments include cells and particularly cultured cells transformed with s-IEMT expression constructs.

Specialized (iso)eugenol-4-O-methyltransferases comprise C. breweri (iso)eugenol-4-O-methyltransferases having amino acid substitutions at one or more of residues 133, 165, 166, 175, 169, 26, 30 and 33. Other specialized (iso)eugenol-4-O-methyltransferases additionally have amino acid substitutions at residue 319. Such s-IEMTs may have increased activity compared with wild-type IEMTs (wt-IEMT) for 4-O-methylation of ferulic acid, caffeic acid, p-coumaric acid, sinapic acid, or their aldehydes, (iso) eugenol, and/or phenylamines.

Preferred specialized (iso)eugenol-4-O-methyltransferases further comprise those having amino acid substitutions at each of residues 133, 165, 175, 166, 169, 26, 30 and 33 as well as s-IEMTs having substitutions at each of residues 133, 165, 175, 166, 169, 26, 30 and 33 and at residue 319. Such s-IEMTs may have increased activity compared with wild-type IEMTs (wt-IEMT) for 4-O-methylation of ferulic acid, caffeic acid, p-coumaric acid, sinapic acid, or their aldehydes, (iso)eugenol, and/or phenylamines. Such s-IEMTs may have increased activity compared with wild-type IEMTs (wt-IEMT) for conversion of 5-hydroxyconiferyl alcohol to iso-sinapyl alcohol.

Individual specialized (iso)eugenol-4-O-methyltransferases are selected from the group consisting of those methyltransferases having amino acid substitutions as follows:

| Specialized (iso)eugenol-4-O-methyltransferases | |
|---|---|
| Name | Amino Acid Substitutions |
| MOMT8-1 | T133L/E165I/F175I/F166W/H169F/M26H/S30R/V33S |
| MOMT8-2 | T133L/E165I/F175I/F166W/H169F/M26S/S30F/V33Y |
| MOMT8-3 | T133L/E165I/F175I/F166W/H169F/M26S/S30F/V33G |
| MOMT9-1 | T133L/E165I/F175I/F166W/H169F/M26H/S30R/V33S/T319M |

Nucleic acids encoding and expression vectors for expressing the various specialized (iso)eugenol-4-O-methyltransferases are contemplated embodiments. The nucleic acid sequences encoding the s-IEMTs have been incorporated into expression vectors for production of the encoded s-IEMT from the s-IEMT expression vector constructs. The expression vector constructs may be designed and adapted for expression in plants, for expression in plant cell cultures, for expression in microorganisms, for expression in insect or mammalian cells and for expression in coupled in vitro transcription/translation systems. The expressed s-IEMTs may function in vivo to alter the lignin biosynthetic pathway when expressed in plants selected from Arabidopsis, corn, switchgrass, poplar and other angiosperms and gymnosperms. The s-IEMTs so expressed may also generate significant levels of chemicals for use as precursors or intermediates in production of various chemicals from renewable resources (i.e., plants and/or cultured cells). In isolated, purified form the s-IEMTs may be used in vitro as catalysts for methylation of substrates of interest.

Expression of the s-IEMTs in plant cell culture is useful for more facile isolation of small molecules, such as methylated ferulic acid and/or iso-sinapyl alcohol. Microorganisms, including but not limited to bacteria and yeast, transformed with expression vector constructs designed to express an s-IEMT, are also candidates for producing chemicals and chemical feedstocks unique to the expressed s-IEMT.

s-IEMTs and their catalyzed reactions can be used as structural components of dedicated modules in synthetic biology approach to reconstruct novel pathways for producing methylated aromatic derivatives Each of such expression cultures, in particular those of plant cell cultures or microorganism cultures, may also be sources for production of an s-IEMT for use in chemical processing. The expressed s-IEMT may be expressed in a fusion form for ready and facile purification, for example, by expressing the s-IEMT in frame with a purification tag, such as a his-tag, a strep-tag, a GST-tag, or the like as are well known in the art. The isolated, purified s-IEMT may be used in vitro to convert chemical intermediates such as the conversion of ferulic acid to a methylated-ferulic acid. Additional as yet untested activities of the s-IEMTs may be sufficiently elevated to carry out other useful chemical conversions.

Exemplifications

CASTing Mutagenesis Libraries of the m-IEMT MOMT-5 to Generate s-IEMTs

Saturation mutagenesis was performed at sites 130, 131, 133, 134, 139, 164, 165, 166, 175, 186, 319, 326 and 327 of IEMT (GenBank U86760.1) (SEQ ID NO. 1) following the QuikChange® site-directed mutagenesis strategy (Stratagene) using NNK degenerate primers (N represents a mixture of A, T, G, C, and K for G/T) (see Bhuiya, M. W. and Liu, C. J. (2010) J. Biol. Chem. 285:277-285, the contents of which, including supplemental materials, are incorporated herein by reference). The codon NNK has 32-fold degeneracy and encodes all 20 amino acids without rare codons.

The modified IEMT (m-IEMT) previously designated MOMT-5 (T133L/E165I/F175I/F166W/H169F where the amino acid residue numbers correspond to those of SEQ ID NO. 1) was subjected to further structural analysis. Crystal structures of MOMT-5 in complex with either coniferyl alcohol or sinapyl alcohol were determined and analyzed. Based on structural information of binding pocket of MOMT-5, amino acid sites for CASTing were chosen and four (4) libraries constructed. The amino acids targeted by CASTing were Met-26/Ser-30/Val-33 for one library; Pro- 129/Leu-133 for a second library; Ala-134/Leu-139 for the third library; and Phe-166/His-169 for the fourth library.

The first library examined amino acid substitutions at positions not previously explored, i.e., Met-26, Ser-30 and Val-33. The specialized (iso)eugenol-4-O-methyltransferase (s-IEMT) having all of the MOMT-5 substitutions and the additional substitution of His for Met at position 26, Arg for Ser at 30 and Ser for Val at 33 was designated MOMT8-1. The ratio of its activity for methylation of p-coniferyl alcohol versus methylation of p-sinapyl alcohol was 7.5:1 whereas the ratio of activity of MOMT-5 was about 4.2:1.

Further shaping of the substrate binding pocket targeting residues Thr-319, Ile-165, Leu-133 and Leu-143 by Iterative Saturation Mutagenesis using MOMT8-1 as the starting point lead to the generation of MOMT9-1 which carried all of the substitutions of MOMT8-1 and an additional substitution of Met for Thr at position 319. Thus MOMT9-1 is a specialized (iso)eugenol-4-O-methyltransferase (s-IEMT) having 6-fold higher specific activity with coniferyl alcohol as the substrate compared to its specific activity with sinapyl alcohol as substrate. The s-IEMT designated MOMT9-1 comprises a specialized (iso)eugenol-4-O-methyltransferase having the following substitutions: T133L/E165I/F175I/F166W/H169F/M26H/S30R/V33S/T319M where amine acid residue numbers correspond to those of SEQ ID NO. 1.

Each of the s-IEMTs was isolated following expression in bacterial cells of nucleic acid sequences encoding the enzymes. The isolated enzymes were analyzed for their substrate versatility, specificity and enzyme kinetics on various phenolic substrates.

The versatile substrate specificities of MOMT9-1 are shown in Table 1:

TABLE 1

Substrate specificity of MOMT9-1

| Substrate | Specific activity (nmol · mg$^{-1}$ · min$^{-1}$) |
|---|---|
| Coniferyl alcohol (CA) | 68.3 ± 0.3 |
| Sinapyl alcohol (SA) | 12.1 ± 0.6 |
| Coniferaldehyde | 5.8 ± 0.2 |
| Sinapaldehyde | 5.0 ± 0.1 |
| p-Coumaryl alcohol | 3.7 ± 0.1 |
| p-Coumaraldehyde | 1.0 ± 0.0 |
| Caffeyl alcohol | 12.9 ± 0.0 |
| Isoeugenol | 268 ± 17 |

Examination and comparison of the enzyme kinetics of various modified and specialized (iso)eugenol-4-O-methyltransferases indicated that the catalytic efficiency ($k_{cat}/K_m$) of MOMT9-1 for coniferyl alcohol was about 25-fold higher than for sinapyl alcohol, whereas that of MOMT8-1 was about 13-fold higher and that of MOMT-5 was less than 3-fold higher, Table 2.

TABLE 2

Summary of enzyme kinetics

| | | Vmax (nmol · mg$^{-1}$ · min$^{-1}$) | $k_{cat}(s^{-1})$ | Km(μM) | $k_{cat}$/Km |
|---|---|---|---|---|---|
| MOMT-5 | CA | 96.1 ± 3.8 | 0.069 ± 0.009 | 11.4 ± 1.6 | 6053 |
| | SA | 46.6 ± 1.5 | 0.033 ± 0.001 | 14.7 ± 2.3 | 2245 |
| MOMT8-1 | CA | 68.1 ± 1.6 | 0.049 ± 0.001 | 16.1 ± 1.3 | 3043 |
| | SA | 8.5 ± 0.3 | 0.006 ± 0.000 | 26.3 ± 4.1 | 228 |
| MOMT9-1 | CA | 88.4 ± 1.7 | 0.063 ± 0.001 | 16.1 ± 1.4 | 3913 |
| | SA | 24.2 ± 0.3 | 0.017 ± 0.0002 | 109.5 ± 4.0 | 155 |

Interestingly MOMT9-1 further appeared to have a significantly increased specific activity for methylation of ferulic acid as shown in Table 3.

TABLE 3

Specific activity with ferulic acid as the substrate

| | nmol/min/mg |
|---|---|
| MOMT-5 | 7.84 |
| MOMT8-1 | 5.10 |
| MOMT9-1 | 50.27 ± 0.33 |

Additional specialized (iso)eugenol-4-O-methyltransferases having eight (8) amino acid substitutions showed enhanced capacity to form iso-sinapyl alcohol by 4-O-methylation of 5-hydroxyl coniferyl alcohol (5-OHCA). Iso-synapyl alcohol is thought to have the potential to be incorporated into lignin. These two additional specialized IEMT's having eight amino acid substitutions are designated as follows and have the indicated substitutions:

MOMT8-2: T133L/E165I/F175I/F166W/H169F/M26S/S30F/V33Y

MOMT8-3: T133L/E165I/F175I/F166W/H169F/M26S/S30F/V33G

The specific activity of the various m-IEMT (MOMT-5) and s-IEMTs (MOMT8-2 and MOMT8-3) are shown in Table 4 and enzyme kinetic analysis is shown in Table 5.

TABLE 4

Specific activity with 5-hydroxyl coniferyl alcohol

| | Specific activity (nmol · mg$^{-1}$ · min$^{-1}$) iso-sinapyl alcohol |
|---|---|
| MOMT-5 | 43.5 ± 4.0 |
| MOMT8-2 | 49.9 ± 0.7 |
| MOMT8-3 | 58.6 ± 0.9 |

TABLE 5

Enzyme kinetics

| | Substrate | Vmax (nmol · mg$^{-1}$ · min$^{-1}$) | $k_{cat}$(s$^{-1}$) | Km(μM) | $k_{cat}$/Km |
|---|---|---|---|---|---|
| MOMT-5 | 5-OHCA | 100.7 ± 3.8 | 0.072 ± 0.003 | 105.0 ± 11.2 | 685.7 |
| | CA | | | | |
| | SA | | | | |
| MOMT8-2 | 5-OHCA | 123.3 ± 8.1 | 0.088 ± 0.006 | 57.9 ± 13.0 | 1519.9 |
| | CA | 32.2 ± 0.8 | 0.023 ± 0.001 | 15.9 ± 1.7 | 1446.5 |
| | SA | 37.9 ± 2.8 | 0.027 ± 0.002 | 35.2 ± 9.8 | 767 |
| MOMT8-3 | 5-OHCA | 145.4 ± 8.7 | 0.104 ± 0.006 | 65.4 ± 13.0 | 1590.2 |
| | CA | 73.5 ± 1.8 | 0.053 ± 0.001 | 23.3 ± 2.4 | 2274 |
| | SA | 51.5 ± 3.8 | 0.036 ± 0.003 | 35.9 ± 9.8 | 1002 |

Incorporation of s-IEMT Variants in Plants

To further explore whether the 4-O-methylation of monolignols perturbs the oxidative radical generation and coupling in situ for lignin polymerization, the specialized IEMT enzymes may be expressed in transformed *Arabidopsis* and poplar using the wild type IEMT and a loss-of-function mutant variant (E165R) as the controls. All genes may be driven by a PAL2 promoter, which controls the expression of phenylalanine ammonium lyase, the first key enzyme in phenylpropanoid-lignin biosynthetic pathway or any type of xylem cell specific expression gene promoters. The expression of transgenes in both T1 and T2 generations may be examined by RT-PCR and qRT-PCR.

Lignin and the related phenolics, which, under UV light produce a typical blue autofluorescence, can be examined in cross sections of the first internode of the stem under epi-fluorescence microscopy. The intensity of autofluorescence, and the layers of fluorescent cells within the interfascicular fibers and vascular bundle of xylem of the transgenic lines may reveal the integrity of the lignin composition versus control stems. When cross-sections are stained with phloroglucinol-HCl reagent, which produces a red/purplish color reaction with hydroxycinnamaldehyde end groups in lignin and thus is used conventionally for monitoring the total lignin, weaker staining in the plants carrying an s-IEMT may show reduced lignin content. In addition, the Mäule staining may enable differentiation between lignin S subunits (showing red) from G subunits (brown) sections of overexpressing plants. These histochemical data will suggest whether the total lignin content in s-IEMT overexpression lines is reduced.

To determine quantitative alteration of lignin deposition as the consequence of the expression of the s-IEMTs, the T2 generations of independent transgenic lines may be grown with the control plants side by side and used for analyzing lignin content and compositions. The total lignin content is quantified using acetyl bromide method. The lignin reduction may be quantified by this method. Changes in lignin composition or structural variability may be revealed by diagnostic thioacidolysis or nuclear magnetic resonance spectroscopy.

The secondary cell walls of monocot grasses and some dicot species including *Arabidopsis thaliana* contain significant quantities of hydroxycinnamates, primarily ferulic acid and p-coumaric acid. These hydroxycinnamates, the so-called "wall-bound" phenolics, mostly link to the C5 carbon of the arabinosyl side chain of arabinoxylans through an ester bond. The bound ferulate residues can dimerize or polymerize with each other, or with other cell-wall polyphenolics presumably via oxidative coupling as does lignin polymerization to form ester-to-ether linkages that cross-link the adjacent polysaccharides, lignins, and/or structural proteins. It is also suggested that polysaccharide-bound ferulate esters may act as nucleation sites for the lignin polymers that anchor lignins to polysaccharides via ether bonds.

Cutinized and suberinized tissues of terrestrial plants, which provide a protective surface barrier, contain substantial amounts of apoplastic aliphatic polymers and small amounts of hydroxycinnamic acids, mainly ferulic acid, p-coumaric acid, sinapic acid and caffeic acid, which may be involved in cross-linking the aliphatics or cross-linking the aliphatics to the cell wall polysaccharides. The specialized (iso)eugenol-4-O-methyltransferases disclosed herein may methylate each of these compounds and thereby may alter the capacity of these aromatic constituents to participate in generating the protective surface barriers.

Expressing the s-IEMTs, in particular the ferulic acid-active s-IEMT designated MOMT9-1, in plants, including grasses, may have considerable effect on the accumulation of wall-bound phenolics provided the s-IEMT also actively methylates ferulic acid and coniferyl alcohol in planta. Wall-bound phenolics may be examined after mild alkaline treatment of cell wall materials.

In addition to lignin and "wall-bound" phenolics, we may examine the polysaccharide cellulose and hemicellulose content of the cell wall of transgenic plants.

Saccharification assays may be used to evaluate the acceptability of cell walls of the s-IEMT plants for bioconversion to products. The samples are exposed to cellulases and other enzymes that specifically hydrolyze cell wall carbohydrates. Control plants and transgenic plants will be compared.

Target plants for incorporation of genes for expression of the s-IEMTs may include but are not limited to *Arabidopsis*, corn, switchgrass, poplar and other angiosperms and gymnosperms.

Successful incorporation and expression of the specialized enzymes may modify the complexity and amounts of lignin in the modified plants, such that the plants may provide an improved source of biomass for conversion to biofuels. Additionally, expression of such specialized IEMTs may create reservoirs of useful chemicals and chemical feedstocks. For example, 4-O-methylation of ferulic acid or caffeic acid, for example by the s-IEMT identified herein as MOMT9-1, could potentially remove them from the lignification pathway and increase their availability for conversion to other down-stream chemicals. While lignin formation in plant cell culture is not a particular issue, the expression of an s-IEMT in plant cells in culture provides an additional opportunity for convenient production of novel phenolic and aromatic compounds.

Additional embodiments include the incorporation and expression of the various s-IEMT in organisms besides plants, particularly microorganisms and other cultured cells. Organisms and cultured cells of choice include bacteria and yeast, plant cell cultures, insect cell cultures and mammalian cell cultures.

Additional embodiments contemplated herein include the use of the s-IEMTs as isolated enzyme constituents in chemical transformations for the production of useful chemicals. The isolated specialized enzymes are useful in reactions in solution and may also be immobilized in continuous, flow through-type production schemes.

The invention claimed is:

1. A specialized (iso)eugenol 4-O-methyltransferase (s-IEMT) enzyme comprising amino acid substitutions at each of residues 133, 165, 175, 166, 169, 26, 30 and 33, where the amino acid residues correspond to those of SEQ ID NO. 1.

2. The s-IEMT of claim 1 further comprising an amino acid substitution at residue 319 of SEQ ID NO. 1.

3. The s-IEMT enzyme of claim 2 selected from the group consisting of s-IEMTs comprising the amino acid substitutions T133L/E165I/F175I/F166W/H169F/M26H/S30R/V33S;
T133L/E165I/F175I/F166W/H169F/M26S/S30F/V33Y;
T133L/E165I/F175I/F166W/H169F/M26S/S30F/V33G; and
T133L/E165I/F175I/F166W/H169F/M26H/S30R/V33S/T319M.

4. An isolated nucleic acid sequence comprising a sequence encoding a specialized (iso)eugenol 4-O-methyltransferase enzyme having amino acid substitutions at each of residues 133, 165, 175, 166, 169, 26, 30 and 33 of SEQ ID NO. 1.

5. The isolated nucleic acid sequence of claim 4 further comprising an amino acid substitution at residue 319 of SEQ ID NO: 1.

6. The isolated nucleic acid sequence of claim 5 selected from the group consisting of sequences encoding an s-IEMT having the amino acid substitutions T133L/E165I/F175I/F166W/H169F/M26H/S30R/V33S;
T133L/E165I/F175I/F166W/H169F/M26S/S30F/V33Y;
T133L/E165I/F175I/F166W/H169F/M26S/S30F/V33G; and
T133L/E165I/F175I/F166W/H169F/M26H/S30R/V33S/T319M.

7. A plant transformed with an expression vector adapted for expression in plants of the specialized IEMT enzyme encoded by the nucleic acid sequence of claim 4 or claim 5.

8. The plant of claim 7 selected from the group consisting of *Arabidopsis*, corn, switchgrass, poplar, angiosperms and gymnosperms.

9. An expression vector adapted for expression in cultured cells of the specialized IEMT enzyme encoded by the nucleic acid sequence of claim 4 or claim 5.

10. The expression vector of claim 9 wherein the cultured cells are selected from the group consisting of cultured bacterial, yeast, plant, insect and mammalian cells.

11. An isolated purified (iso)eugenol 4-O-methyltransferase (s-IEMT) obtained from the cultured cells of claim 10.

12. An isolated purified (iso)eugenol 4-O-methyltransferase (s-IEMT) obtained from the plant claim 7.

* * * * *